United States Patent [19]
Angeletakis et al.

[11] Patent Number: 6,121,344
[45] Date of Patent: Sep. 19, 2000

[54] OPTIMUM PARTICLE SIZED HYBRID COMPOSITE

[75] Inventors: Christos Angeletakis, Orange; Alvin I. Kobashigawa, Laguna Beach, both of Calif.

[73] Assignee: Kerr Corporation, Orange, Calif.

[21] Appl. No.: 09/270,999

[22] Filed: Mar. 17, 1999

Related U.S. Application Data

[60] Provisional application No. 60/089,859, Jun. 19, 1998.

[51] Int. Cl.[7] .............................. A61K 6/083; C08K 3/36
[52] U.S. Cl. ........................ 523/116; 523/115; 524/493; 524/559; 526/320; 526/326
[58] Field of Search .................................. 523/115, 116; 524/493, 559; 526/326, 320

[56] References Cited

U.S. PATENT DOCUMENTS

| | | |
|---|---|---|
| Re. 35,264 | 6/1996 | Bennett . |
| 3,792,531 | 2/1974 | Rossi . |
| 3,893,840 | 7/1975 | Wason . |
| 4,059,232 | 11/1977 | Engels . |
| 4,117,981 | 10/1978 | Engels . |
| 4,129,261 | 12/1978 | Engels et al. . |
| 4,132,806 | 1/1979 | Wason . |
| 4,156,766 | 5/1979 | Feldt . |
| 4,157,920 | 6/1979 | Wason et al. . |
| 4,161,455 | 7/1979 | Wason . |
| 4,177,563 | 12/1979 | Schmitz-Josten et al. . |
| 4,202,813 | 5/1980 | Wason . |
| 4,215,033 | 7/1980 | Bowen . |
| 4,260,454 | 4/1981 | Wason et al. . |
| 4,303,205 | 12/1981 | Geiger et al. . |
| 4,336,245 | 6/1982 | Wason . |
| 4,375,967 | 3/1983 | Schaefer . |
| 4,380,432 | 4/1983 | Orlowski et al. . |
| 4,422,880 | 12/1983 | Wason et al. . |
| 4,496,106 | 1/1985 | Gross . |
| 4,503,169 | 3/1985 | Randklev . |
| 4,544,359 | 10/1985 | Waknine ................................. 523/116 |
| 4,551,486 | 11/1985 | Tateosian et al. . |
| 4,558,825 | 12/1985 | John et al. . |
| 4,609,687 | 9/1986 | Schwabe et al. . |
| 4,711,913 | 12/1987 | Tateosian et al. . |
| 4,793,809 | 12/1988 | Sigler et al. . |
| 4,801,528 | 1/1989 | Bennett . |
| 4,813,875 | 3/1989 | Hare . |
| 4,846,165 | 7/1989 | Hare et al. . |
| 4,863,977 | 9/1989 | Tateosian et al. . |
| 4,936,775 | 6/1990 | Bennett . |
| 4,978,640 | 12/1990 | Kelly . |
| 5,055,497 | 10/1991 | Okada et al. . |
| 5,062,577 | 11/1991 | Schmitt et al. . |
| 5,065,946 | 11/1991 | Nishida et al. . |
| 5,133,508 | 7/1992 | Stehr et al. . |
| 5,177,120 | 1/1993 | Hare et al. . |
| 5,210,109 | 5/1993 | Tateosian et al. . |
| 5,211,748 | 5/1993 | Robinson et al. . |
| 5,218,070 | 6/1993 | Blackwell . |
| 5,221,202 | 6/1993 | James . |
| 5,335,867 | 8/1994 | Stehr et al. . |
| 5,338,773 | 8/1994 | Lu et al. . |
| 5,502,087 | 3/1996 | Tateosian et al. . |
| 5,547,379 | 8/1996 | Hasel . |
| 5,548,000 | 8/1996 | Nagel et al. ............................. 523/212 |
| 5,554,030 | 9/1996 | Ario et al. . |
| 5,556,038 | 9/1996 | Nakamura et al. . |
| 5,595,487 | 1/1997 | Ario et al. . |
| 5,604,626 | 2/1997 | Teowee et al. . |
| 5,609,675 | 3/1997 | Noritake et al. . |
| 5,610,712 | 3/1997 | Schmitz et al. . |
| 5,612,414 | 3/1997 | Becker et al. . |
| 5,616,650 | 4/1997 | Becker et al. . |
| 5,637,641 | 6/1997 | Becker et al. . |
| 5,710,194 | 1/1998 | Hammesfahr et al. . |
| 5,733,997 | 3/1998 | Becker et al. . |
| 5,750,628 | 5/1998 | Becker et al. . |
| 5,767,218 | 6/1998 | Becker et al. . |
| 5,807,954 | 9/1998 | Becker et al. . |
| 5,837,752 | 11/1998 | Shastri et al. . |
| 5,838,483 | 11/1998 | Teowee et al. . |
| 5,936,006 | 8/1999 | Rheinberger et al. ................... 523/116 |
| 5,990,195 | 11/1999 | Arita ................................... 528/502 C |

OTHER PUBLICATIONS

Cabot Corporation, *CAB–O–SIL TS–530 Treated Fumed Silica,*, Technical Data, Jul. 1989.

Dennis Miller, Cabot Corporation, *CAB–O–SIL® Fumed Silica Properties and Functions*, pp. 3–5 (no date available).

Degussa Corporation, *Technical Data for AEROSIL® Types* (no date available).

S. Inokoshi, "*Posterior Restorations: Ceramics or Composites?*", Transactions Third International Congress on Dental Materials, Ed. H. Nakajima, Y. Tani JSDMD (Nov. 1997).

*Primary Examiner*—Andrew E. C. Merriam
*Attorney, Agent, or Firm*—Wood, Herron & Evans, L.L.P.

[57] ABSTRACT

The present invention provides a dental composite which has the high strength required for load bearing restorations, yet maintains a glossy appearance, even after substantial wear. Through the use of particles having a mean particle size between about 0.05 μm and about 0.50 μm, the composite is useful in stress bearing restorations and in cosmetic restorations. The structural filler used is typically ground to a mean particle size of less than 0.5 μm and also includes a microfill having a mean particle size less than 0.05 μm to improve handling and mechanical characteristics. The preferred dental composites maintain their surface finish even after substantial use and also have the strength properties of hybrid composite resins. The structural filler is ground, typically by agitator milling, to the preferred particle size.

18 Claims, 2 Drawing Sheets

OPTIMUM PARTICLE SIZED HYBRID COMPOSITE

Pursuant to 37 C.F.R. § 1.78(a)(4), this application is a continuation of, claims the benefit of and priority to prior filed co-pending Provisional Application Number 60/089,859, filed Jun. 19, 1998, which is expressly incorporated herein by reference.

FIELD OF THE INVENTION

The present invention is generally related to a composite resin material used for dental restoration, and more particularly to a universal composite resin material suitable for all dental restorations incorporating a uniformly dispersed submicron sized reinforcing particulate which provides high strength, improved wear resistance and gloss retention in clinical use.

BACKGROUND OF THE INVENTION

In dentistry, practitioners use a variety of restorative materials in order to create crowns, veneers, direct fillings, inlays, onlays and splints. Composite resins are a type of restorative material which are suspensions of strengthening agents, such as mineral filler particles, in a resin matrix. These materials may be dispersion reinforced, particulate reinforced, or hybrid composites.

Dispersion reinforced composites include a reinforcing filler of, for example, fumed silica having a mean particle size of about 0.05 $\mu$m or less, with a filler loading of about 30%–45% by volume. Because of the small particle size and high surface area of the filler, the filler loading into the resin is limited by the ability of the resin to wet the filler. Consequently, the filler loading is limited to about 45% by volume. Due to the low loading, the filler particles are not substantially in contact with one another. Thus, the primary reinforcing mechanism of such dispersion reinforced composites is by dislocation of flaws in the matrix around the filler. In dispersion reinforced materials, the strength of the resin matrix contributes significantly to the total strength of the composite. In dentistry, dispersion reinforced composite resins or microfills are typically used for cosmetic restorations due to their ability to retain surface luster. Typically, these microfill resins use free radical-polymerizable resins such as methacrylate monomers, which, after polymerization, are much weaker than the dispersed filler. Despite the dispersion reinforcement, microfill resins are structurally weak, limiting their use to low stress restorations.

One example of a dispersion reinforced composite is HELIOMOLAR®, which is a dental composite including fumed silica particles on the order of 0.05 $\mu$m mean particle size and rare earth fluoride particle on the order of less than 0.2 $\mu$m mean particle size. HELIOMOLAR® is a radiopaque microfill-type composite. The rare earth fluoride particles contribute to both flexural strength and radiopacity.

Particulate reinforced composites typically include a reinforcing filler having an average particle size greater than about 0.6 $\mu$m and a filler loading of about 60% by volume. At these high filler loadings, the filler particles begin to contact one another and contribute substantially to the reinforcing mechanism due to the interaction of the particles with one another and to interruption of flaws by the particles themselves. These particulate reinforced composite resins are stronger than microfill resins. As with the dispersion reinforced composites, the resin matrix typically includes methacrylate monomers. However, the filler in particulate reinforced composites has a greater impact on the total strength of the composite. Therefore, particulate reinforced composites are typically used for stress bearing restorations.

Another class of dental composites, known as hybrid composites, include the features and advantages of dispersion reinforcement and those of particulate reinforcement. Hybrid composite resins contain fillers having an average particle size of 0.6 $\mu$m or greater with a microfiller having an average particle size of about 0.05 $\mu$m or less. HERCULITE® XRV (Kerr Corp.) is one such example. HERCULITE® is considered by many as an industry standard for hybrid composites. It has an average particle size of 0.84 $\mu$m and a filler loading of 57.5% by volume. The filler is produced by a wet milling process that produces fine particles that are substantially contaminant free. About 10% of this filler exceeds 1.50 $\mu$m in average particle size. In clinical use, the surface of HERCULITE® turns to a semi-glossy matte finish over time. Because of this, the restoration may become distinguishable from normal tooth structure when dry, which is not desirable for a cosmetic restoration.

Another class of composites, flowable composites, have a volume fraction of structural filler of about 10% to about 30% by volume. These flowable composites are mainly used in low viscosity applications to obtain good adaptation and to prevent the formation of gaps during the filling of a cavity.

Figure 2A:
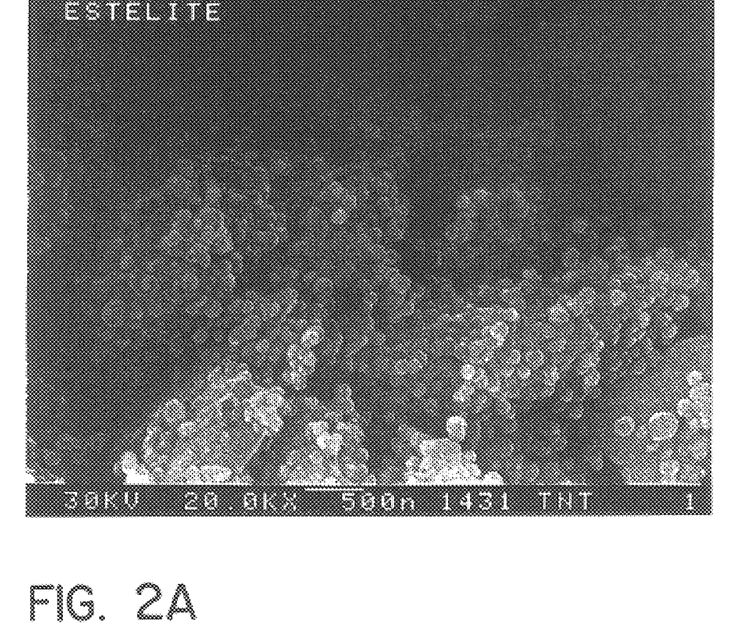
FIG. 2A is a scanning electron micrograph, at 20,000× magnification, of the prior art filler particles formed by sol-gel processes.
Figure 2B:
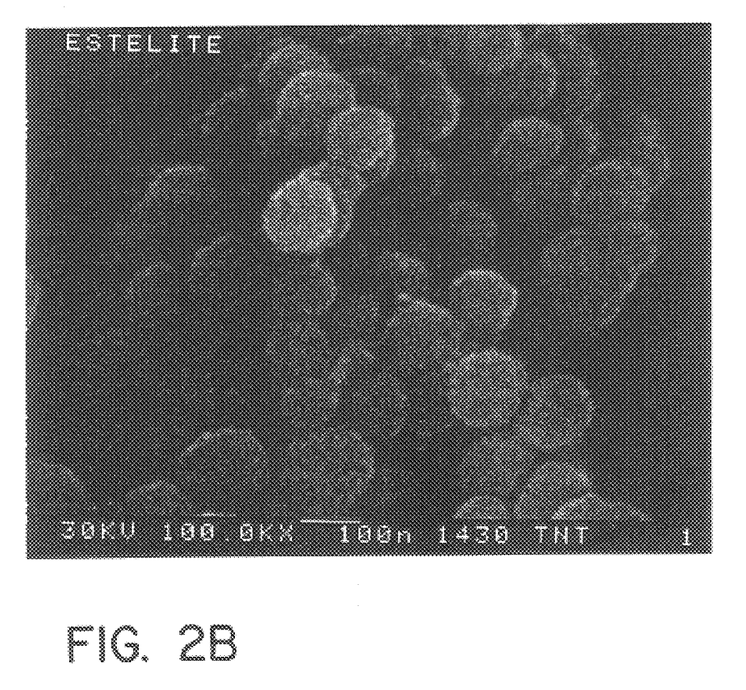
FIG. 2B is a scanning electron micrograph, at 100,000× magnification, of the prior art filler particles formed by sol-gel processes.

Various methods of forming submicron particles, such as precipitation or sol gel methods, are available to produce particulate reinforcing fillers for hybrid composites. However, these methods do not restrict the particle size to at or below the wavelength of light to produce a stable glossy surface. U.S. Pat. No. 5,609,675 to Noritake et al., shows an inorganic filler composition of 60%–99% by weight of spherical oxide particles having a diameter between 0.1–1.0 $\mu$m, and 1%–40% by weight of oxide particles having a mean particle diameter of less than 0.1 $\mu$m. This filler is manufactured by a chemical sol gel process. The particle size range includes particle sizes up to 1.0 $\mu$m and thus a dental composite using such filler will not provide a glossy surface in clinical use. The particles formed by the sol-gel process are spherical as shown in FIGS. 2A and 2B. The formulations described are designed to improve mechanical performance, wear and surface roughness of restorations, but do not provide for the retention of surface gloss in clinical use. Clinical studies of this material have actually shown high wear rates of 22.4 $\mu$m per year, which cannot establish a stable surface (S. Inokoshi, "Posterior Restorations: Ceramics or Composites?" in *Transactions Third International Congress on Dental Materials* Ed. H. Nakajima, Y. Tani JSDMD 1997).

Communication by a milling method may also be used for forming the submicron particles. The predominant types of milling methods are dry milling and wet milling. In dry milling, air or an inert gas is used to keep particles in suspension. However, fine particles tend to agglomerate in response to van der Waals forces, which limits the capabilities of dry milling. Wet milling uses a liquid such as water or alcohol to control reagglomeration of fine particles. Therefore, wet milling is typically used for communication of submicron-sized particles.

A wet mill typically includes spherical media that apply sufficient force to break particles that are suspended in a liquid medium. Milling devices are categorized by the method used to impart motion to the media. The motion imparted to wet ball mills includes tumbling, vibratory, planetary and agitation. While it is possible to form submicron particles with each of these types of mills, the agitation or agitator ball mill is typically most efficient.

The agitator ball mill, also known as an attrition or stirred mill, has several advantages including high energy efficiency, high solids handling, narrow size distribution of the product output, and the ability to produce homogeneous slurries. The major variables in using an agitator ball mill are agitator speed, suspension flow rate, residence time, slurry viscosity, solid size of the in-feed, milling media size and desired product size. As a general rule, agitator mills typically grind particles to a mean particle size approximately 1/1000 of the size of the milling media in the most efficient operation. In order to obtain mean particle sizes on the order of 0.05 µm to 0.5 µm, milling media having a size of less than 0.45 mm can be used. Milling media having diameters of 0.2 mm and about 0.6 mm are also available from Tosoh Ceramics, Bound Brook, N.J. Thus, to optimize milling, it is desired to use a milling media approximately 1000 times the size of the desired particle. This minimizes the time required for milling.

Previously, the use of a milling process to achieve such fine particle sizes was difficult due to contamination of the slurry by the milling media. By using yttria stabilized zirconia (YTZ or Y-TZP, where TZP is tetragonal zirconia polycrystal) the contamination by spalling from the milling media and abrasion from the mill is minimized. Y-TZP has a fine grain, high strength and a high fracture toughness. YTZ is the hardest ceramic and because of this high hardness, the YTZ will not structurally degenerate during milling. High strength Y-TZP is formed by sintering at temperatures of about 1550° C. to form tetragonal grains having 1–2 µm tetragonal grains mixed with 4–8 µm cubic grains and high strength (1000 MPa), high fracture toughness (8.5 MPa m$^{1/2}$) and excellent wear resistance. The use of Y-TZP provides a suitable milling media for providing relatively pure structural fillers having mean particle sizes less than 0.5 µm.

Despite some reduction in contamination of the ground filler particulate by the use of YTZ milling media, presently available agitator ball mills still introduce an unacceptably high level of contamination into dental composites containing the ground filler. No current single dental composite provides the high strength required for use in the wide variety of repairs with the required gloss after substantial clinical use. To achieve these goals, current cosmetic dental restorations require the use of two or more layers of the various composite materials in order to obtain the strength and appearance desired. The present invention eliminates the need for multiple layers of various composite materials.

SUMMARY OF THE INVENTION

The present invention provides a resin-containing dental composite including a structural filler of ground particles having an average particle size of between about 0.05 µm and about 0.5 µm that has the high strength required for load bearing restorations, yet maintains a glossy appearance in clinical use required for cosmetic restorations. Further, because the structural filler particles are ground, the particles are nonspherical, providing increased adhesion of the resin to the structural filler, thereby further enhancing the overall strength of the composite. Through the use of structural filler particles that are ground and that have an average particle size less than the wavelength of light, that is less than about 0.50 µm, the dental composite of the present invention provides the luster and translucency required for cosmetic restorations. Specifically, since the structural filler size is less than the wavelength of visible light, the surface of a dental restoration will reflect more light in some directions than in others even after wear of the composite by brushing. The visible light waves do not substantially interact with the structural filler particles protruding out of the surface of the composite, and therefore, haze is reduced and the luster of the surface is maintained even after substantial brushing.

A known method of milling, agitator milling, has been adapted for use in the field of dental composites. As adapted, this method is capable of further reducing the average particle size of the HERCULITE® filler to an average particle size of between about 0.05 µm and 0.5 µm. The particle size is at or below the wavelength of light, which minimizes interaction with light, thus producing a stable glossy surface in clinical use. The particles are still large enough to reinforce the composite by the particulate reinforcement mechanism, so the restorations are also stress bearing. The number of larger particles, above 0.5 µm in diameter, are also minimized to help produce the stable glossy surface.

Additionally, because the structural filler particles are ground to an average particle size between about 0.05 µm and about 0.50 µm, the particles interact with one another to strengthen the composite, in the manner of typical hybrid composites, to allow a composite of the present invention to be useful in stress bearing restorations.

Figure 1A:
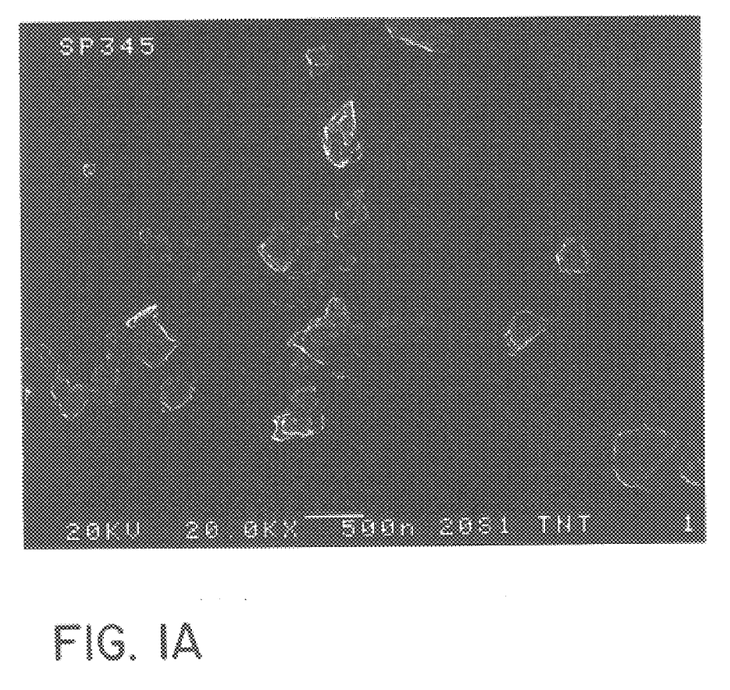
FIG. 1A is a scanning electron micrograph, at 20,000× magnification, of the ground particulate of the present invention.
Figure 1B:
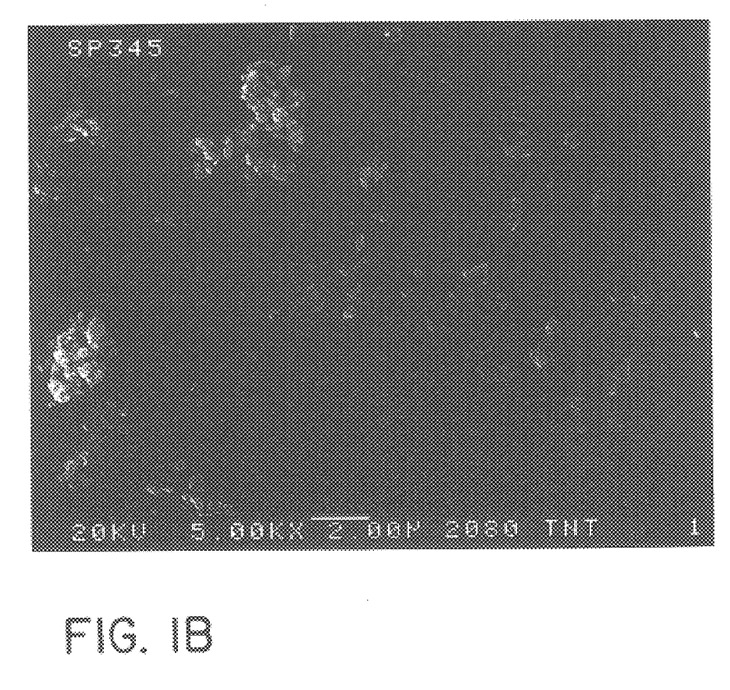
FIG. 1B is a scanning electron micrograph, at 5,0000× magnification, of the ground particulate of the present invention.

In a preferred embodiment, the structural filler is ground, typically by agitator milling, to the preferred mean particle size. As opposed to the particles formed by the known sol-gel process, the grinding of the structural filler results in nonspherical particles which due to their irregular shape interact with the polymerized resin to a much greater extent to increase adhesion of the resin to the structural filler and thereby increase the overall strength of the composite. The irregular shape of the particles is shown in FIGS. 1A and 1B.

Agitator milling with selected media and optimized parameters produces the required size particles, free of contamination in a narrow particle size distribution. This reduces the small percentage of particles above 0.5 µm which can contribute to producing a non-glossy surface in clinical use.

In accordance with a further aspect of the invention, microfill particles having an average particle size less than about 0.05 µm are added, preferably between about 1% by weight and about 15% by weight of the composite. The microfill particles contribute to dispersion reinforcement, fill the interstices between the larger structural filler particles reducing occluded volume, and provide a large surface area to be wetted by the resin to increase strength. The microfill particles also contribute to the flow properties of the uncured resin.

DETAILED DESCRIPTION OF THE INVENTION

The present invention, in a preferred form, is a dental restorative composite which includes a ground structural filler having a mean particle size between about 0.05 μm and about 0.50 μm and a microfill having a mean particle size less than about 0.05 μm in a curable resin, preferably a photopolymerizable resin containing methacrylate monomers. Such methacrylate monomer resins are cured when exposed to blue visible light. The dental composite is applied to teeth by the dental practitioner and exposed to a visible light source to cure the resin. The cured resin has a flexural strength higher than 100 MPa which allows for the use of the resin in stress bearing applications.

To provide ground structural filler having a mean particle size of less than 0.5 μm, an extensive communication step is required. Communication is preferably performed in an agitator mill and more preferably an agitator mill designed to minimize contamination, such as that described in U.S. Pat. No. 6,010,085 entitled "Agitator Mill and Method of Use for Low Contamination Grinding," C. Angeletakis, filed on even date herewith and incorporated herein by reference in its entirety. Communication deagglomerates the structural filler particles by separating particles from clusters, decreases the size of the structural filler particles, eliminates large particles by breakage and increases the specific surface area of the structural filler particles by producing a large quantity of very fine particles. Size reduction with an agitator mill occurs due to a combination of impact with the milling media, abrasion with the milling media and attrition of the particles.

Structural fillers suitable for use in the present invention include barium magnesium aluminosilicate glass, barium aluminoborosilicate glass, amorphous silica, silica-zirconia, silica-titania, barium oxide, quartz, alumina and other inorganic oxide particles.

EXAMPLES

To prepare a structural filler for inclusion into a dental composite, the filler material to be milled, such as barium aluminoborosilicate glass (for example, type SP-345, Specialty Glass, Oldsmar Fla.), is charged into an agitator mill, such as a one-liter total capacity agitator mill from Draiswerke Inc., Mahwah, N.J., type PML-H/V, modified to include a clear polyurethane clad agitator and grinding chamber, a YTZ main seal and a YTZ gap separator as described in U.S. Pat. No. 6,010,085 entitled "Agitator Mill and Method of Use for Low Contamination Grinding," C. Angeletakis, filed on even date herewith and incorporated herein by reference in its entirety.

Three methods (A, B and C) were tested in which the agitator mill was filled to 70% of its volume with Y-TZP media. Method A used milling media with a size of 0.65 mm and Method B used milling media with a size of 0.40 mm. A 20% slurry including 700 grams of 345 mesh (20–30 μm) barium aluminoborosilicate glass in water (SP-345 available from Specialty Glass, Oldsmar, Fla.) was circulated through the mill and to an outside water-cooled bath at 20–30 liters per hour using a peristaltic pump. The agitator mill was operated at a tip speed of 10 m/sec. for 3 hours. In Method C, the ground slurry of Method A was used, and the mill was then charged with 70% of its volume of 0.20 mm Y-TZP milling media, and the milling process was repeated for 1.5 hours. During the milling process, rough edges and facets were created on the structural filler particles by the impact with the milling media, abrasion with the milling media and attrition of the particles. Each of these edges provide an adhesion site for the resin which increases the overall strength of the cured composite.

When the 20% filler slurry is removed from the mill, the mean particle size is measured, typically by laser scattering. Laser scattering is a method of measuring mean particle size by sensing the average relative angular intensity of scattered light. A beam of monochromatic light with a uniform wave front is directed at the sample, the light is diffracted or scattered by the particles and a detector is used to measure the relative average intensity of the scattered light at various angles. The mean particle size and size distribution may then be calculated from the relative average intensity. One such laser scattering device is disclosed in U.S. Pat. No. 5,610,712 to Schmitz et al., incorporated herein by reference in its entirety. For the present example, a Horiba Model 2A-910 Laser Scattering Mean Particle Size Analyzer was used. The particle size range of the structural fillers prepared by methods A, B and C are set forth in TABLE 1, as well as the particle size range for the PRODIGY® (Kerr Corp.) hybrid composite. TABLE 1 shows, for example, that for Method A, 10% by volume of the filler particles have a mean particle size of less than 0.40 μm; 50% by volume of the filler particles have a mean particle size less than 0.62 μm; and 90% by volume of the filler particles have a mean particle size less than 0.82 μm.

TABLE 1

| | Mean Particle Sizes In Microns | | | |
|---|---|---|---|---|
| VOLUME | PRODIGY ® | A | B | C |
| 10% | 0.42 μm | 0.40 μm | 0.27 μm | 0.24 μm |
| 50% | 0.84 μm | 0.62 μm | 0.47 μm | 0.36 μm |
| 90% | 1.50 μm | 0.82 μm | 0.76 μm | 0.61 μm |

The slurry was then dried at 110° C. and the dried cake was sieved through a 100 mesh (150 μm) plastic screen. The ground glass was then silanated by spraying in a V-blender with a 20% hydrolyzed solution of gamma-methacryloxypropyltrimethoxy-silane in water to make the powder hydrophobic. The loading of the silane in the filler was 2.5% by weight.

The properly sized structural filler is combined with colloid sized particles, such as types of silica, alumina and silicates, for example silica zirconia or silica titania, the particles having a mean particle size less than 0.05 μm. Typically, hydrophobic fumed silica is used in an amount between 1–15 wt % of the final composition. As will be shown in TABLE 3, it is possible to use two types of fumed silica such as TS-530 having an average particle size of 0.02 μm and OX-50 having an average particle size of 0.04 μm.

The structural filler and the colloidal fillers are then combined with a light-curable resin base material which may include commercially available monomers containing methacrylate groups. TABLE 2 lists the components of the resin that will be used in later examples. Pigments such as titanium dioxide may be added to control optical properties of the composite.

TABLE 2

| RESIN COMPOSITION | |
|---|---|
| COMPONENT | % BY WEIGHT |
| BisGMA (Bisphenol A Diglycidyl ether dimethacrylate) | 3.0 |
| Trethylene Glycol Dimethacrylate | 24.7 |
| Ethoxylated Bisphenol A Dimethacrylate | 71.1 |
| 2-Ethylhexyl-4-(dimethylamino)benzoate | 0.49 |
| Camphorquinone | 0.17 |
| 2-Hydroxy-4-methoxy Benzophenone | 0.49 |
| (BHT) Butylated Hydroxytoluene | 0.05 |

Other monomers may be used in the resin composition, such as diethylene glycol dimethacrylate, triethylene glycol dimethacrylate, tetraethylene glycol dimethacrylate, 1,6-hexanediol dimethacrylate, 1,12-dodecanediol dimethacrylate, diurethane dimethacrylate (Rohamere 6661-0, Huls America, Somerset, N.J.), trimethylolpropane trimethacrylate, glyceryl dimethacrylate, neopentylglycol dimethacrylate.

The resin is introduced into a planetary mixer thermostated at 50° C. The planetary mixer is then started and the filler containing the physically admixed components listed in TABLE 3 are added slowly over a period of 3 hours. The composite is subsequently mixed for another hour and then de-aerated under attenuated oxygen pressure.

Cured samples having the dimensions of 20 mm×40 mm×2 mm were then prepared. The extended clinical wear of the material was simulated by abrading the samples with 600 grit silicon carbide sandpaper until a constant gloss value was obtained. The surface gloss was then measured using a micro-tri-gloss apparatus (available from BYK-Gardner USA of Columbia, Md.). The micro-tri-gloss apparatus performs a photoelectric measurement of a specularly reflected light from a surface. The micro-tri-gloss instrument was calibrated according to ISO standard 2813 with a measurement of 60°. The results presented in TABLE 4 are the average of three measurements taken.

The OX-50 particles are AEROSIL® OX-50 fumed silica, available commercially from Degussa Corp., Ridgefield Park, N.J. The OX-50 particles have a surface area of 50±15 $m^2$/g and an average agglomerated particle size of 40 nanometers. The OX-50 particle is greater than 99.8 wt % $SiO_2$ with traces of $Al_2O_3$, $Fe_2O_3$, $TiO_2$ and HCl. The OX-50 particles are then silanated by spraying in a V-blender with a 20% hydrolyzed solution of gamma-methacryloxypropyltrimethoxysilane in water to make the powder hydrophobic. The loading of the silane in the filler was 5% by weight.

The CAB-0-SIL TS-530 treated fumed silica is a high purity silica treated with hexamethyldisilazane to make the particles extremely hydrophobic. The CAB-O-SIL particles are fumed silica produced by hydrolysis of silicon tetrachloride vapor in a flame of hydrogen and oxygen. Any hydrogen chloride adsorbed onto the CAB-O-SIL particle during the combustion process is reduced by a calcination (typically to less than 200 ppm HCl).

The colloid filler particles contribute to dispersion reinforcement, fill the interstices between the larger structural filler particles which reduces occluded volume, provide a large surface area to be wetted by the resin and therefore increases strength. The use of the colloidal fillers reduces polymer shrinkage and allows a match between the modulus of elasticity and the coefficient of thermal expansion of the composite with that of the tooth. The improved adhesion coupled with the control of the polymer shrinkage, the modulus of elasticity and the coefficient of thermal expansion reduces micro-leakage of bacteria along the bond interface between the tooth and the cured dental composite.

In forming a restoration using the composite of the present invention, the surface of the tooth is prepared by removing any portion of the tooth enamel, and if necessary the dentin, that is decayed or damaged. A retention groove is then formed in the dentin if needed to maintain the restoration on the tooth. The practitioner then adds opacifiers and pigments to match the color of the composite with the color of the tooth. The composite is then built up on the surface of the tooth to replace any lost material. Once the practitioner is satisfied with the appearance of the restoration the composite is exposed to a visible light source to cure the resin and activate the adhesive by cross-linking the polymer matrix. After the composite has been cured, the surface is polished.

The mean particle size of the structural filler is limited to less than the wavelength of light to prevent the structural filler from decreasing surface gloss after substantial brushing. However, it is expected that as the particle size is reduced below about 1 µm the strength needed for load bearing restorations demises due to increasing occluded volume of resin. Currently, it is believed that a mean particle size between about 0.05 µm and about 0.5 µm provides the best balance between optical and structural properties.

The following examples were prepared using particles ground in the manner discussed above.

Example A

A resin composite was prepared by mixing:

27.6% by weight of Resin (Table 2);

63.7% by weight of silanated barium aluminoborosilicate (SP-345) structural filler having a mean particle size of 0.62 µm as prepared by Method A, discussed above;

5.0% by weight silanated OX-50 fumed silica having an average particle size of 0.04 µm; and 3.7% by weight TS-530 hydrophobic fumed silica having an average particle size of 0.02 µm.

The above components were thoroughly mixed as discussed above and samples were prepared in the manner discussed below.

Example B

A resin composite was prepared by mixing:

28.2% by weight of Resin (Table 2);

64.7% by weight of silanated barium alurninoborosilicate (SP-345) structural filler having a mean particle size of 0.47 µm as prepared by Method B, discussed above;

3.1% by weight silanated OX-50 fumed silica having an average particle size of 0.04 µm; and 3.9% by weight TS-530 hydrophobic fumed silica having an average particle size of 0.02 µm.

The above components were thoroughly mixed as discussed above and samples were prepared in the manner discussed below.

Example C

A resin composite was prepared by mixing:

29.2% by weight of Resin (Table 2);

65.2% by weight of silanated barium aluminum silicate (SP345) structural filler having a mean particle size of 0.36 µm as prepared by Method C, discussed above; and 2.3% by weight silanated OX-50 fumed silica having an average particle size of 0.04 µm; and 3.3% by weight TS-530 hydrophobic fumed silica having an average particle size of 0.02 µm.

The above components were thoroughly mixed as discussed above and prepared in the manner discussed below.

Testing

In testing the strength of the dental composite, standard ISO methods such as the ISO 4049 test for resin-based filling materials were used whenever possible. Cured samples of the composite pastes were prepared with the dimensions of 20×40×2 mm. The samples were sanded with #600 silicon carbide paper under water until a constant gloss value was obtained. The gloss of the surface of the above composites was measured using a Micro-Tri-Gloss apparatus (BYK-Gardner USA, Columbia, Md.) which performs a photoelectric measurement of specularly reflected light from a surface. This instrument was calibrated according to ISO standard 2813. The measurement angle was 60 degrees. An average of three measurements is reported. The ISO 4049 standard considers a value of 100 % Al to be a minimum value for a radiopaque composite. A value of 200 % Al or greater is preferred by practitioners to properly determine the position of the restoration.

In TABLE 3, the properties of the dental composites of EXAMPLES A, B, and C are compared with the PRODIGY® hybrid composite. The hybrid composite (PRODIGY®) has a flexural strength over 100 MPa, which allows its use in stress bearing restorations. The composites of EXAMPLES A, B, and C each have a flexural strength above 100 MPa, approaching that of the PRODIGY® composite, which allows their use in stress bearing restorations. As can also be seen in TABLE 3, the flexural modulus for the composites of EXAMPLES A and C is 9,248 MPa, which approaches the modulus of the PRODIGY® composite. The Rockwell hardness, which is similar for the four composites reported in TABLE 3, is an average of 3 measurements on the surface of a cylindrical sample 10 mm in diameter and 4 mm in height. The composites were light cured for 40 seconds and stored in water for 24 hours at 37° C. prior to the hardness measurement. Despite the similarity in the mechanical properties of the PRODIGY® restorative and the EXAMPLE A, B and C restoratives, after 24 hours of brushing, the glossy appearance of the PRODIGY® material is lost leaving a matte finish as occurs in normal clinical use.

In TABLE 4, the properties of the dental composite of EXAMPLE B are compared to the commercially available products PALFIQUE ESTELITE® (from Tokoyama), HELIOMOLAR® (from Vivadent), SILUXPLUS® (from 3 M), and DURAFIL® (from Kulzer). Despite high surface gloss and translucency, these commercial composites do not have the strength required for load bearing restorations, while the composite of the present invention does have sufficient strength.

TABLE 3

Physical Properties of Small Particle Composites (SD)

|  | PRODIGY ® | EXAMPLE A | EXAMPLE B | EXAMPLE C |
|---|---|---|---|---|
| Resin wt % | 23 | 27.6 | 28.2 | 29.2 |
| Mean Particle Size of Ground Filler | 0.84 μm | 0.6 μm | 0.47μm | 0.35 μm |
| Ground Barium aluminum silicate, SP-345, wt % | 69.4 | 63.7 | 64.7 | 65.2 |
| 40 nm silanated Silica, OX-50, wt % | 3.5 | 5 | 3.1 | 2.3 |
| 20 nm hydrophobic Silica, TS-530, wt % | 4.1 | 3.7 | 3.9 | 3.3 |
| Load Weight % | 77 | 72.4 | 71.8 | 70.8 |
| Load Volume % | 57.5 | 51.6 | 50.7 | 49.3 |
| Flexural Strength (MPa) | 136 | 122 | 105 | 111 |
|  | (18) | (9) | (14) | (7) |
| Flexural Modulus (MPa) | 10,960 | 9,248 | 8801 | 9,248 |
|  | (744) | (522) | (720) | (522) |
| Compressive Strength (MPa) | 367 | 366 | 312 | 368 |
|  | (52) | (23) | (40) | (42) |
| Rockwell Hardness 15T | 83.3 | 80.1 | 80.4 | 77.5 |
| Depth of Cure 40 s (mm) | 5.5 | 4.7 | 4.3 | 4.3 |
| Consistency-Slump (cm) | 2.5 | 2.7 | 1.6 | 1.7 |
| Gloss, 60 degrees | 19.6 | 30.1 | 46.7 | 45.8 |
|  | (0.3) | (0.8) | (0.3) | (0.1) |

TABLE 4

Physical Property Comparison of Fine Particle Composite with Commercial Composites (SD)

|  | EXAMPLE B | PALFIQUE ESTELITE ® (TOKOYAMA) | HELIOMOLAR ® (VIVADENT) | SILUX PLUS ® (3M) | DURAFIL ® (KULZER) |
|---|---|---|---|---|---|
| Load Weight % | 71.8 | 69 | 67 | ca50 | ca50 |
| Load Volume % | 50.7 | ca45 | 44 | ca38 | ca38 |
| Flexural Strength (MPa) | 105 | 78 | 92 | 79 | 83 |
|  | (14) | (8) | (13) | (10) | (12) |
| Flexural Modulus (MPa) | 8801 | 6690 | 6,277 | 7,000 | 5,325 |
|  | (720) | (500) | (388) | (639) | (301) |
| Compressive Strength (MPa) | 312 | 357 | 279 | 248 | 428 |
|  | (40) | (25) | (81) | (96) | (47) |
| Rockwell Hardness 15T | 80.4 | 80.6 | 77.0 | 81.7 | 76.9 |
| Depth of Cure 40 s (mm) | 4.3 | 4.2 | 4.4 | 4.4 | 5.5 |

TABLE 4-continued

Physical Property Comparison of Fine Particle Composite with Commercial Composites (SD)

|  | EXAMPLE B | PALFIQUE ESTELITE ® (TOKOYAMA) | HELIOMOLAR ® (VIVADENT) | SILUX PLUS ® (3M) | DURAFIL ® (KULZER) |
|---|---|---|---|---|---|
| Consistency-Slump (cm) | 1.6 |  | 2.7 | 4.3 | 2.7 |
| Gloss, 60 degrees | 46.7 | 46.9 | 40.4 | 41.4 | 41.5 |
|  | (0.3) | (0.2) | (0.5) | (0.5) | (1.1) |
| Radiopacity (% Al) | 210 | 175 | 200 | 0 | 0 |

Thus, the dental composite of the present invention provides a restoration having the high strength useful for load bearing restorations and also provides translucency and surface gloss, useful in cosmetic restorations. The gloss is apparent even after substantial wear as can be observed in a recall appointment 6 months or longer after the placement of the restoration. Through the use of structural filler particles having a mean particle size less than the wavelength of light, yet large enough to provide strength, the dental composite of the present invention provides the luster and translucency of dispersion reinforced composites with the strength of hybrid composites.

While the present invention has been illustrated by a description of various embodiments and while these embodiments have been described in considerable detail, it is not the intention of the Applicants to restrict or in any way limit the scope of the appended claims to such detail. Additional advantages and modifications will readily appear to those skilled in the art. The invention in its broader aspects is therefore not limited to the specific details and representative composition as shown and described. This has been a description of the present invention, along with the preferred composition using the present invention as currently known. However, the invention itself should only be defined by the appended claims.

What is claimed is:

1. A dental composite, comprising:
    a resin base; and
    about 10% by volume to about 80% by volume filler consisting essentially of a ground structural filler and a microfiller,
    wherein the ground structural filler comprises between about 10% by volume and about 70% by volume of the composite and consists of ground particles of mean particle size between about 0.05 $\mu$m and about 0.50 $\mu$m, and wherein the ground structural filler contains less than 50% by volume of particles above 0.5 $\mu$m in diameter, and
    wherein the microfiller comprises up to about 10.0% by volume of the composite and consists of particles of mean particle size of about 0.04 $\mu$m or less.

2. The dental composite of claim 1, wherein the cured resin composite has a flexural strength of at least 70 MPa.

3. The dental composite of claim 2, wherein the cured resin composite has a flexural strength of at least 100 MPa.

4. The dental composite of claim 1, wherein the cured resin composite maintains surface gloss after wear.

5. The dental composite of claim 1, wherein the resin base comprises a polymerizable vinyl compound.

6. The dental composite of claim 1, wherein the ground structural filler contains less than 10% by volume of particles above 0.8 $\mu$m in diameter.

7. The dental composite of claim 1, wherein the microfiller comprises between about 1.0 and about 10.0% by volume of the composite.

8. The dental composite of claim 7, wherein the microfiller consists of particles having a mean particle size of approximately 0.04 $\mu$m which comprise between about 0.5% by volume and about 5.0% by volume of the composite and particles having a mean particle size of approximately 0.02 $\mu$m which comprise between about 0.5% by volume and about 5.0% by volume of the composite.

9. The dental composite of claim 1, wherein the cured resin composite has a gloss at a 60° measurement angle of about 45 or greater.

10. The dental composite of claim 1, wherein the cured resin composite has a gloss at a 60° measurement angle of about 30 or greater.

11. The dental composite of claim 1, wherein the cured resin composite has a radiopacity of at least about 100% Al.

12. The dental composite of claim 1, wherein the cured resin composite has a radiopacity of at least about 200 % Al.

13. A dental composite comprising:
    a resin base; and
    about 11% by volume to about 80% by volume filler in the resin base, the filler consisting essentially of a ground structural filler and a microfiller,
    wherein the ground structural filler comprises between about 10% by volume and about 70% by volume of the composite and consists of ground particles having a mean particle size of between about 0.05 $\mu$m and about 0.50 $\mu$m, and
    wherein the microfiller comprises between about 1.0% by volume and about 10.0% by volume of the composite and consists of particles having a mean particle size of about 0.04 $\mu$m or less, and
    wherein the cured resin composite has a flexural strength greater than about 100 MPa.

14. The dental composite of claim 13, wherein the cured resin composite has a gloss at a 60° measurement angle of about 30 or greater and a flexural strength of about 105 MPa or greater.

15. The dental composite of claim 14, wherein the cured resin composite has a gloss at a 60° measurement angle of about 45 or greater.

16. The dental composite of claim 13, wherein the resin base includes a polymerizable vinyl compound.

17. The dental composite of claim 13, wherein the resin base includes Bis-phenol-A-bis-(2-hydroxy-3-methacryloxypropyl) ether; Triethyleneglycoldimethacrylate; and Ethoxylated bis-phenol-A-dimethacrylate.

18. A dental composite comprising:
    a resin base including bis-phenol-A-bis-(2-hydroxy-3-methacryloxypropyl) ether, triethyleneglycoldimethacrylate, and ethoxylated bis-phenol-A-dimethacrylate;
    about 11% by volume to about 80% by volume filler in the resin base, the filler consisting essentially of a ground structural filler and a microfiller, wherein the ground structural filler comprises between about 10% by volume and about 70% by volume of the composite and consists of ground particles having a mean particle size between about 0.05 µm and about 0.50 µm and wherein the microfiller comprises between about 0.5% by volume and about 5.0% by volume of the composite with particles consisting of a mean particle size of approximately 0.04 µm; and wherein the microfiller further comprises between about 0.5% by volume and about 5.0% by volume of the composite with particles consisting of a mean particle size of approximately 0.02 µm, the cured dental composite having a surface gloss at a 60° measurement angle of at least about 30 after simulated extended clinical wear.

* * * * *

UNITED STATES PATENT AND TRADEMARK OFFICE
CERTIFICATE OF CORRECTION

PATENT NO.    : 6,121,344
DATED         : September 19, 2000
INVENTOR(S)   : Angeletakis et al.

It is certified that error appears in the above-identified patent and that said Letters Patent is hereby corrected as shown below:

Title page,
Item [56], References Cited, OTHER PUBLICATIONS, "Sllica" should be
-- Silica --.

Column 2,
Line 50, "Communication" should be -- Comminution --.
Line 58, "communication" should be -- comminution --.

Column 5,
Line 12, "communication" should be -- comminution --.
Line 13, "Communication" should be -- Comminution --.
Line 19, "Communication" should be -- Comminution --.

Column 8,
Line 35, "alurninoborosilicate" should be -- aluminoborosilicate --.

Signed and Sealed this

Nineteenth Day of November, 2002

Attest:

JAMES E. ROGAN
Attesting Officer    Director of the United States Patent and Trademark Office